United States Patent [19]
Hughes

[11] Patent Number: 6,158,676
[45] Date of Patent: *Dec. 12, 2000

[54] MICRO-ATOMIZING DEVICE

[75] Inventor: Nathaniel Hughes, Palm Springs, Calif.

[73] Assignee: Hughes Technology Group, L.L.C., Palm Springs, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/878,648

[22] Filed: Jun. 19, 1997

Related U.S. Application Data

[60] Provisional application No. 60/020,177, Jun. 21, 1996.

[51] Int. Cl.$^7$ ..................................................... B05B 7/04
[52] U.S. Cl. ......................... 239/405; 239/403; 239/337
[58] Field of Search ..................... 239/401, 406, 239/8, 337, 405, 403; 128/200.14, 200.18, 200.21

[56] References Cited

U.S. PATENT DOCUMENTS

| | | | |
|---|---|---|---|
| 622,245 | 4/1899 | Luttrell | 239/406 |
| 721,900 | 3/1903 | Lassoe et al. | 239/406 |
| 1,770,232 | 7/1930 | Fegley | 239/401 |
| 3,163,362 | 12/1964 | McFee | 209/401 |
| 4,241,877 | 12/1980 | Hughes | 239/405 |
| 4,453,542 | 6/1984 | Hughes | 128/200 |
| 4,595,143 | 6/1986 | Simmons et al. | 239/406 |
| 5,513,798 | 5/1996 | Tavor | 239/8 |

*Primary Examiner*—Lesley D. Morris
*Attorney, Agent, or Firm*—Jenkens & Gilchrist

[57] ABSTRACT

The micro-atomizing device of the present invention creates high energy vortices. These high speed vortices are generated simultaneously and synchronously and then merged into a three dimensional force field. When the high energy vortices are brought together, a large vacuum is produced in a resultant stable vortex force field in a vortex accumulation zone. The high vacuum draws the fluid to be atomized through a delivery tube into the vortex accumulation zone. The high energy within the vortex accumulation zone either breaks up the fluid to be atomized into very small droplets or gasifies the fluid by the combination of high energy density cold boiling, shockwave generated ultrasound, and centripetal forces.

26 Claims, 9 Drawing Sheets

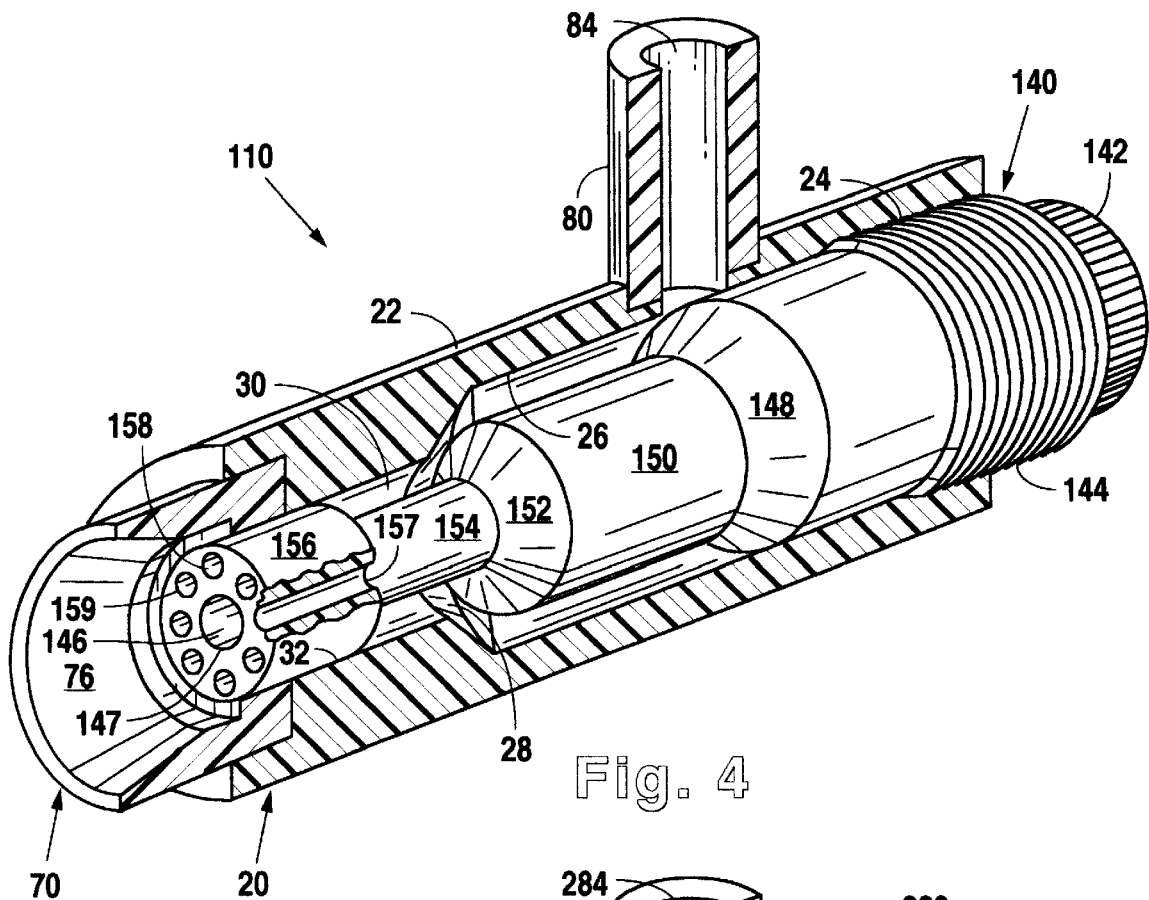
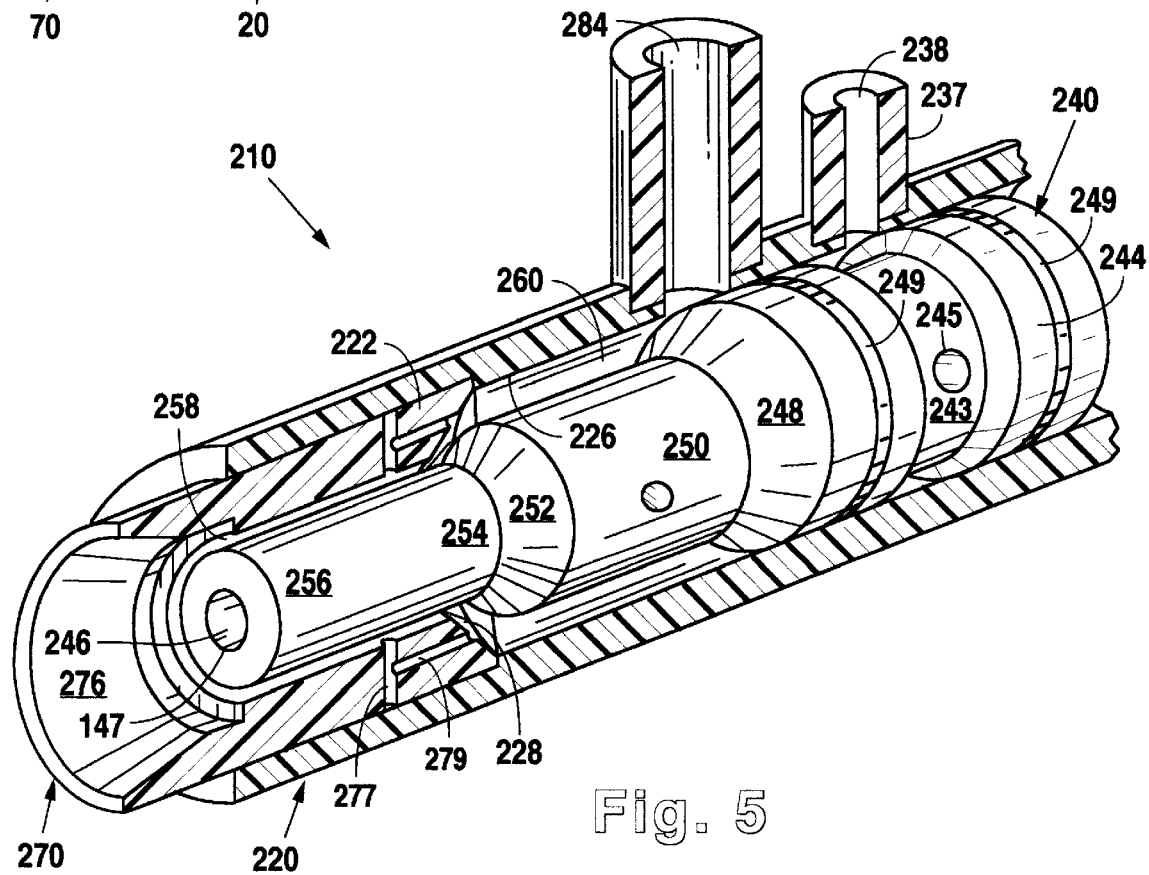

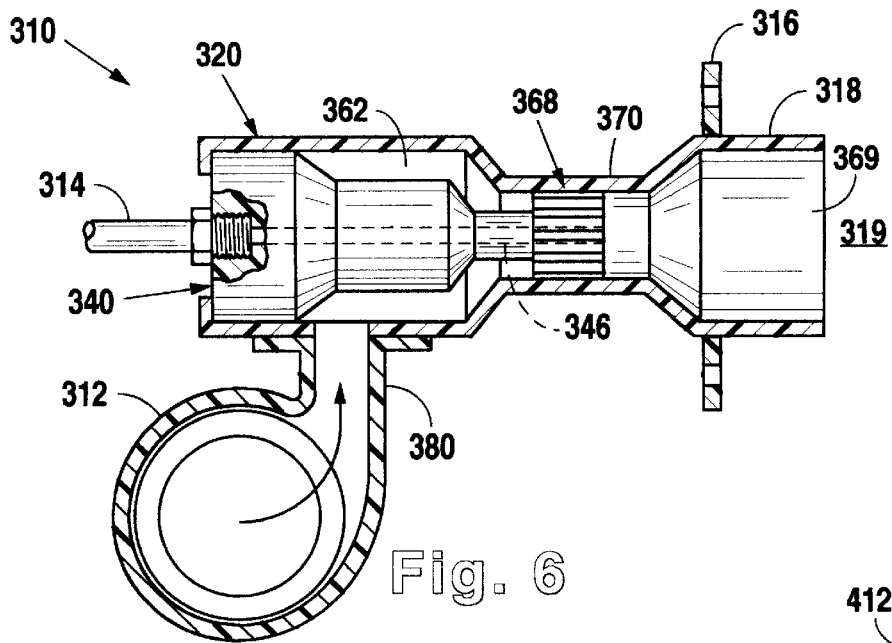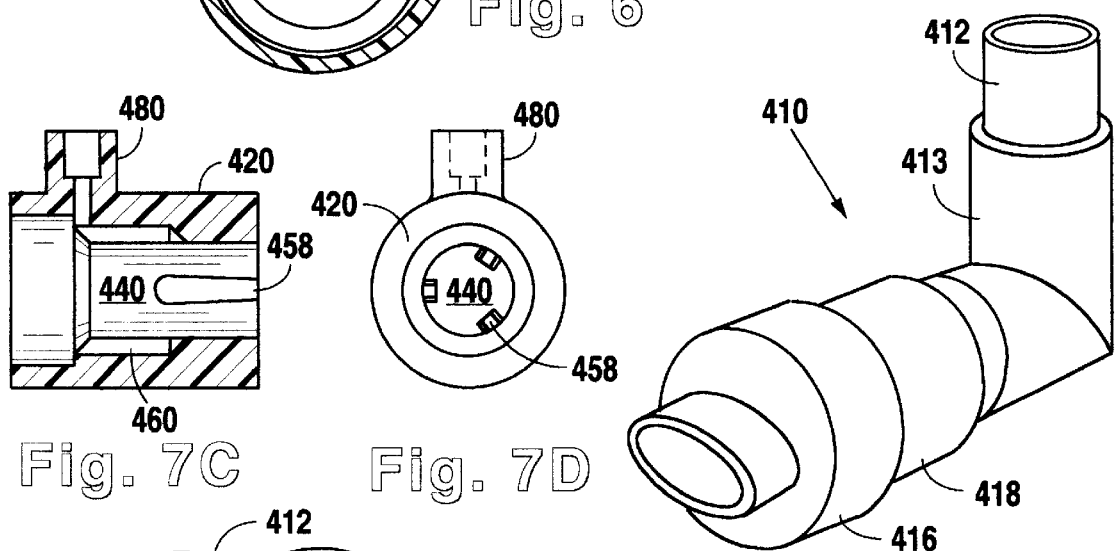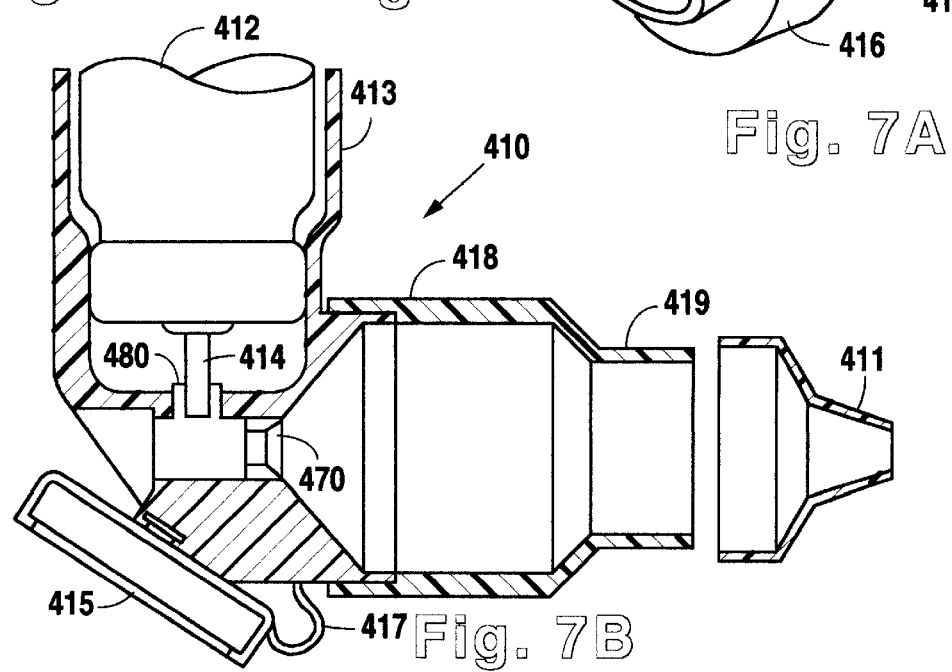

MICRO-ATOMIZING DEVICE

This application claims the benefit of U.S. Provisional Application Serial No. 60/020,177 filed Jun. 21, 1996.

Field of the Invention

The present invention pertains to micro-atomizers; more particularly, the present invention pertains to highly efficient gas-driven devices which utilize vortex energy in a maximized, high energy density, stable force field. Additionally heat may be added to provide additional energy to micro-atomize or gasify liquids or to aerosolize flowable solids. Micro-atomization defines very small micron size droplets having a uniform or monodispersed character.

Background

The process of micro-atomization or subdivision of a liquid, gas droplets, or aerosolization or dispersion of a flowable solid is quite complex. In most prior art gas-powered mechanical atomizers, the liquid or gas to be atomized or flowable solid to be dispersed must first be provided with sufficient pressure energy and then caused to jointly pass through the geometry of a mechanical atomizer so that they may be pushed through one or more shear orifices. Such shear orifices are typically formed in a plate having a plurality of small holes, which small holes subdivide or disperse the flow by shear effects caused by high flow velocity. On the output side of these prior art atomizers, the actual break-up or dispersion of the flowing substance produces a very broad range of droplet sizes or a "bell shaped" droplet distribution curve.

The devices utilizing this invention generally produce monodispersed low micron-size droplets which are a vaporous "gaseous like" cloud having large surface area. This is a very desirable result for most processes where micro-atomization is employed. Most other prior art atomizers produce a large droplet size distribution, which large droplet size distribution may be described by a bell shaped curve spanning a large droplet size range. In the present invention, the micro-atomization of liquids or gases will produce a significant drop in the temperature of the liquid being atomized due to the micro-atomization and vortex phenomena as the heat energy in the liquid is transferred efficiently and absorbed by the vortex process. The substance being atomized can actually be changed completely into gaseous form. For example, some micro-atomization systems may change a liquid into gas.

Uniquely, as opposed to prior art mechanical atomizers, the following is inherent in the micro-atomization process embodied the present invention.

(1) In the disclosed micro-atomizer, embodiments utilizing the present invention the gas powerant or propellant only passes through the vortex energy forming geometries, not both the propellant gas and the liquid to be atomized as in most other prior art designs. This separation of the propellant and the liquid to be atomized prevents clogging, denigration of efficiency and a reduction in the energy burden placed on the micro-atomizer device. The only exception is when the device is used for aerosol duty with liquified gas propellants as is in metered drug delivery devices.

(2) Unlike all other prior art atomization systems, the pressure of the powerant propellant gas is not critical. Heat or thermal energy can be substituted for or added to the process. The vector cross product of pressure times mass flow times BTU, if heat is used, is totally used by the atomizers of the present invention; not just pressure as in prior art mechanical shear atomizers.

(3) Viscosity and density of the liquid to be atomized dramatically affect the performance of all other prior art shear atomizers. Viscosity and density of the liquid to be atomized have little or no effect on the vortex micro-atomizing process of the present invention.

The need to micro-atomize a flowing substance is found in many and diverse fields. In health care, respiratory medication must be micro-atomized to effectively reach the alveolar tissue in the lungs. In manufacturing processes, the combination of paints or coatings with reduced solvents or water-based solutions can only be done by the efficient micro-atomization of the paint or coating. In food processing, atomized coatings are applied to both preserve and effectively flavor foods. In the burning of fuel, much more efficient and cleaner combustion can be obtained when fuel is micro-atomized. In electronics, the uniform application of micro-atomized photo-resistive materials in the lithography process which is used to manufacture integrated circuits and micro-chips is critical. In environmental applications, it may be necessary to increase humidity by spraying water into ambient air or to scrub stack gases by injecting a spray of a special chemical into a discharge line. There are few applications where micro-atomization is not beneficial.

Future uses of micro-atomized fluids will permit lubricants to be applied to machine surfaces heretofore unlubricated. Atomizing refrigerants will increase the efficiency of cooling operations; especially with environmentally safe propellants. Pollutants or salt will more easily be removed from water by micro-atomization and fluids heretofore thought to be uncombinable or difficult to combine can be mixed together using the micro-atomization techniques of the present invention.

Prior art efforts to improve and create atomization techniques have included high pressure shear atomizers, air assist atomizers and ultra high pressure hydraulic nozzles. While such devices have improved the state of the art, these prior art devices are still subject to the limitations of the other prior art atomizers already described. Such problems have included a high pressure energy requirement to impart sufficient pressure and velocity energy to the substance to be atomized to accomplish the desired atomization; clogging of the passages within the atomizing device guiding the flow of gas and liquid; and variation in size and dispersion of the droplets. In addition, the utilization of all prior art atomizing devices is, as previously noted, severely limited by the viscosity and density of the fluid to be atomized. Fluid viscosity has an exponential effect on the difficulty of micro-atomizing fluids in prior art atomizers. Fluid density further lowers the efficiency of most prior art atomizing devices.

Accordingly, there remains a need in the art for a micro-atomization devices which can micro-atomize fluids over a wide viscosity and density range with no penalty, which can produce droplets of substantially uniform size, which is not subject to clogging and which has low energy requirements. Such devices should also be inexpensive and easy to manufacture. The devices described herein which utilize the present invention utilize easy to manufacture geometries, which enable simple methods of creating small openings without using high precision drilling techniques or exotic molding techniques.

SUMMARY

The micro-atomization devices of the present invention are useable with fluids over a wide viscosity and density range, and do not, in most all cases, place the fluid to be atomized within the passages in the device and are self-cleaning. In most cases, there is no liquid involved in the vortex formation process. The micro-atomization devices of the present invention have universally low power requirements, are inexpensive, are easy to manufacture, and perform over wide ranges. Their use over a wide range permits the use of broad computerized application design techniques for various applications.

The micro-atomization devices of the present invention operate by creating a three dimensional stable vortex shockwave force field. This three dimensional stable vortex shockwave force field is created by using a coherent synchronous family of stable vortex generators and vortex energy concentrators. The fluid or flowable solid to be atomized is drawn through a centrally located flow passage within the family or array of stable vortex generators and vortex energy concentrators into a vortex accumulation zone containing the three dimensional stable vortex force field. In the vortex accumulation zone the fluid is micro-atomized in an open geometric space and dispersed by the extremely high energies created by the vortex shockwave force field.

Construction of the micro-atomization devices of the present invention is effected by ringing the centrally located flow passage used for fluid transport with an array or a plurality of vortex generators. The vortex generators terminate at a vortex energy concentrator. The family or array of vortex concentrators is a group of cylindrical or other uniformly geometrically shaped passages. Upstream of the vortex concentrators are the basic vortex generators. Once the vortices are formed by the vortex generators, vorticity is always conserved. The vortices then pass through the vortex concentrators and come together in a highly efficient manner in a prescribed vortex accumulation zone. The high vacuum formed by the confluence of vortices and resultant high speed rotation in the vortex accumulation zone draws the fluid to be atomized through the centrally located flow passage. Shockwaves within the vortices due to supersonic flow enter the vortex accumulation zone and causes the fluid to be atomized to gasify by cold boiling, shockwave energies, and centripetal forces. The fluid is then micro-atomized by being formed into micron size liquid droplets which are generally monodispersed. Flowable solids can be aerosolized also by the same process.

In the preferred embodiment a "dumbbell" shaped vortex generating rod assembly is mounted within a hollow housing. Stable vortices are formed in the space between the vortex rod assembly and the hollow housing. As these vortices pass through the vortex concentration delivery tubes, these vortex concentration delivery tubes concentrate and substantially enhance the fully formed vortex energy to a significantly higher energy level. These vortices increase rotational energy intensity (i.e. rotational speed) due to conservation of angular momentum and the conservation of vortex energies in such an area change process. These vortices also have vastly increased energy density due to energy availability per unit volume or area. Upon exiting the vortex concentration tubes the vortices come together to form a three dimensional stable vortex force field in the vortex energy accumulation zone. The vortex energy accumulation zone is a properly designed open space integral to a specially designed vortex accumulation resonant chamber.

The number of vortex generators on the periphery of the vortex rod assembly depends on the mass of gas available to power the micro-atomizer by forming vortices therein, the amount of fluid to be micro-atomized and the energy density desired (watts/cm$^3$) to achieve the desired level of micro-atomization. There can be three to 100 or more such vortex generators.

The instant invention is an energy conversion device. It converts modest amounts of mass flow and pressure energies and thermal energy into vortical form in Stage One of the process. In Stage Two of the process, the invention uniquely concentrates these energies through conservation of angular momentum, preservation of vorticity, and multiple area transformations in very high speed vortices and supersonic shockwaves which shockwaves are combined in very high energy density, high velocity streams. In Stage Three of the process, the various energy streams are synergistically efficiently combined in the vortex energy accumulation zone. High energy density and the unique combination of energies is the key factor in the energy conversion process utilized in the present invention.

BRIEF DESCRIPTION OF THE FIGURES

A better understanding of the micro-atomizing device of the present invention may be had by reference to the figures wherein:

FIG. 4 is a perspective view in partial section of a micro-atomizer having a multi-ported dumb bell vortex rod assembly;

FIG. 5 is a perspective view in partial section of micro-atomizer having an annular vortex delivery passage;

FIG. 6 is a cross-sectional view of a micro-atomizer according to the present invention used to enhance the combustion of fuels;

FIG. 7A is a perspective view of a metered dose inhaler micro-atomizer according to the present invention used to deliver medicaments powered by aerosol or compressed gas propellants and which delivers medicaments and propellant together;

FIG. 7B is a cross-sectional view of the atomizer shown in FIG. 7A;

FIG. 7C is an enlarged view of the vortex formation zone of the atomizer shown in FIG. 7B;

FIG. 7D is an end view of the atomizer shown in FIG. 7C;

OPERATION

Figure 1:
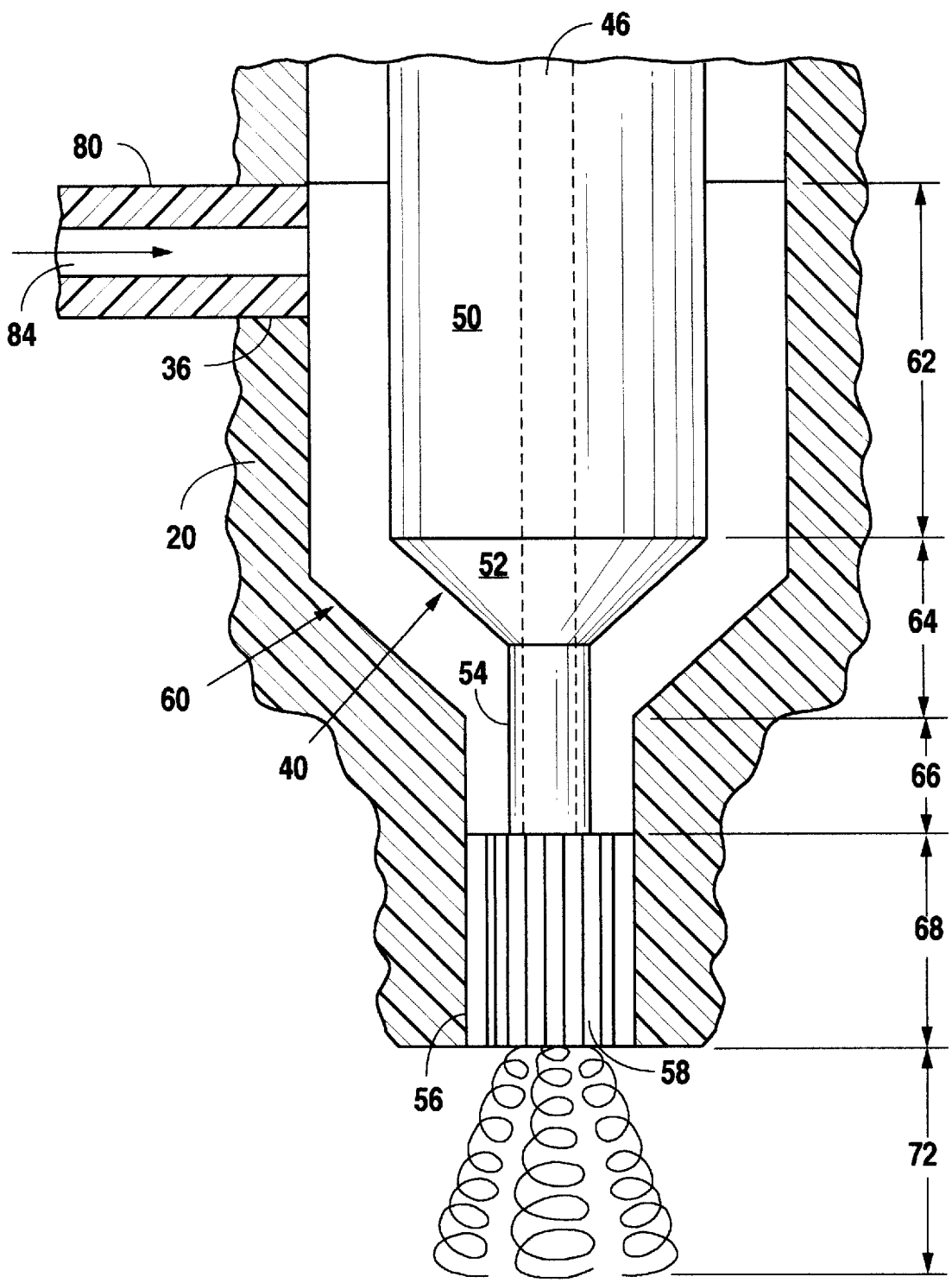
FIG. 1 is an elevational view in partial section of the operative portion of a micro-atomizer according to the present invention.
Figure 2A:
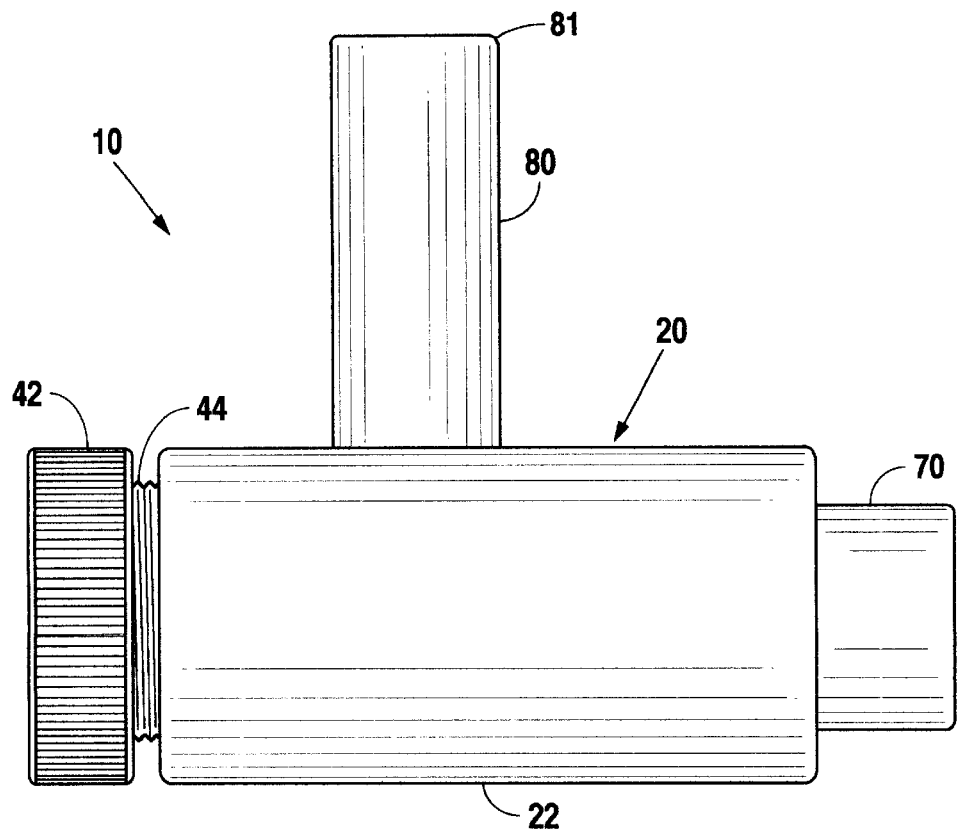
FIG. 2A is an elevational view of the exterior of a micro-atomizer having a straight inlet.
Figure 2B:
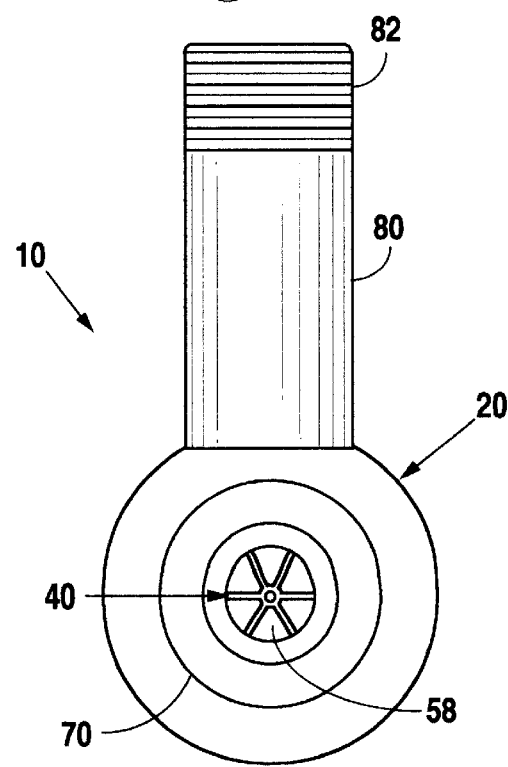
FIG. 2B is a right side end view of the micro-atomizer as shown in FIG. 2 except for a threaded inlet.
Figure 2C:
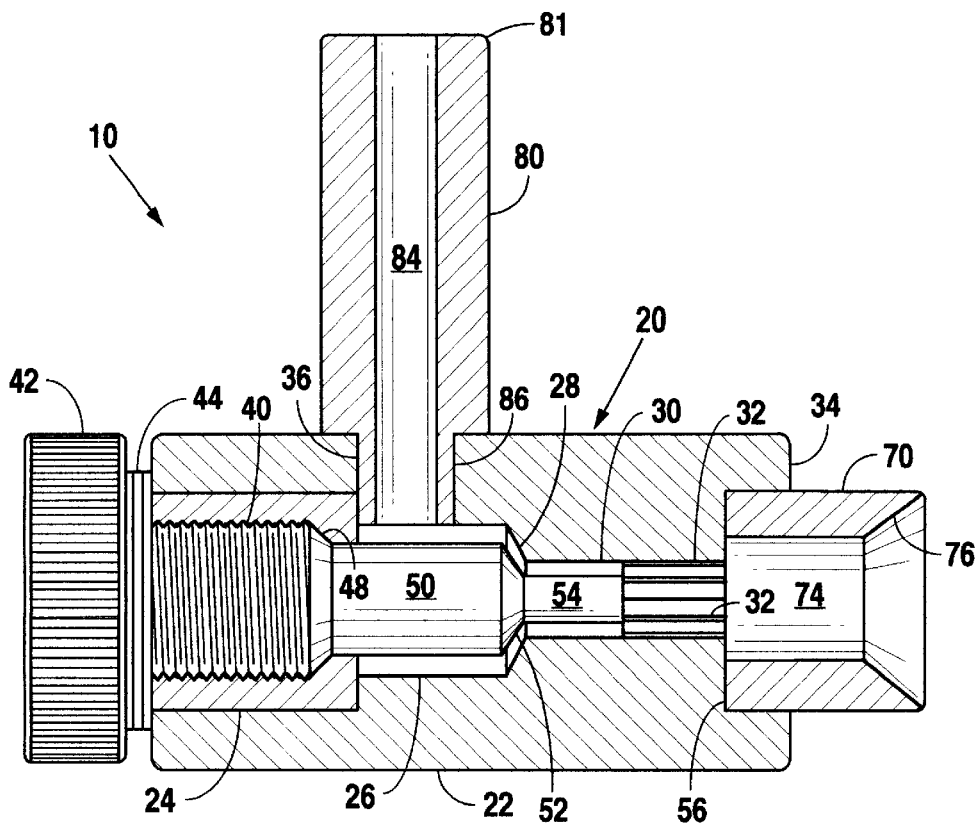
FIG. 2C is a cross-sectional view of the micro-atomizer shown in FIG. 2A.

The present invention is based upon the creation of a powerful, stable, rotating vortex force field by generating a large number of synchronously concurrent, rotating, small, high energy intense vortices. These small, high energy intense vortices are then transported through very small vortex energy density concentration and shockwave generating tubes before being combined into a large powerful vortex force field. The small, high energy intense vortices revolve at a very high speed and have a maximum energy density due to their tight geometries and are aided and abetted by a high frequency ultrasonic pulse due to the linear supersonic speeds of the individual vortices, and the resultant shockwaves produced. The frequency of the ultrasonic pulse is inversely proportional to the port diameter and the inlet to outlet area ratio.

The area ratio between the vortex forming chamber and vortex concentration orifices, and the diameter of the vortex concentration tubes determine the energy density magnification, rotation velocities, linear velocity, supersonic shockwave strength, and oscillating frequency.

By combining the high speed and supersonic shockwaves of the individual vortices, a powerful ring of vortices is created at the exit of the concentration passageways through which the individual vortices are transported. This powerful ring of vortices then turns into a three-dimensional vortex force field which has a high rotational speed and produces a resultant high vacuum. This high vacuum allows for super "cold boiling" of the liquids to be atomized. The micro-atomization process begins because all liquids include trapped gases at atmospheric pressure. It is the trapped gases which erupt powerfully when exposed to high vacuums and then the liquids to be atomized are further processed by the confluence of the individual vortices and the high velocity shockwave pulses. The process of micro-atomization is regulated and made complete by the supersonic shockwave pulse which is further enhanced as the individual vortices come together. All the fluids to be atomized are then subjected to complete micro-atomization, which micro-atomization is further enhanced by the centripetal forces present from rotation of the vortices in the vortex accumulation zone.

APPLIED THEORY

As may be seen in FIG. 1, the flow of the vortex forming fluid through inlet 80 impinges on the upstream end of the dumb bell shaped vortex forming rod assembly 50 in the interior chamber 60 of the nozzle body assembly 20. The impingement of the flow of the vortex forming fluid on the large dumb bell shaped nozzle rod assembly 40 and the specialized geometry and the resulting right angle turn of the vortex forming fluid sets the vortex generating action of the high velocity vortex forming fluid into rotational motion within the vortex formation zone 62. A large multiplicity of smaller vortices is thus generated. The generated smaller vortices then pass into a vortex concentration zone 64 where they are intensified and unified before traveling through the vortex organization zone 66. From the vortex organization zone 66, the smaller vortices pass into the vortex delivery passages or the vortex energy amplification and concentration channels 58, in the vortex energy concentration zone 68. Within the channels 58 the vortices intensify in rotational and linear velocity. In addition, supersonic flow occurs and shockwaves are formed. When the vortical flows exit the vortex delivery passages 58 they come together in the vortex accumulation zone 72. In the vortex accumulation zone 72 a three dimensional powerful rotating vortex force field is created. Vorticity is always preserved, and the vortex and shockwave energies commingle with high efficiency and integration.

The intensification of the vortex action and the accompanying high vacuum and supersonic shockwaves in the vortex accumulation zone 72 results from the following four factors:

First, the conservation of angular momentum within the vortex forming fluid increases the speed of the individual vortices as they each enter the vastly smaller volume of the individual vortex delivery tubes 58. Specifically, a 50 to 100-fold increase in the rotational speed of each individual vortex may occur in each of the vortex delivery tubes 58, due to area ratios between the two zones, and the preservation of vorticity.

Second, since energy must be conserved, the vastly reduced volume of the individual vortex delivery tubes 58 acts as a fluidic motion amplifier for any existing vortices. This fluidic motion amplification produces a much higher energy density vortex flow in each tube 58 than in the vortical flows which exist upstream, before the vortex forming fluid passes through the individual vortex delivery tubes 58.

Third, the supersonic shockwaves found within each vortex tube 58 are produced by the efficient acceleration of the gas to supersonic speeds and the absence of boundary layer separation expansion of the jets to these supersonic speeds due to the centripetal force support created by the high speed vortical activity in each tube 58. Thus, increased vorticity and high frequency shockwaves are produced by the small volume of the multiple vortex delivery tubes 58 in concert with the energy conservation of angular momentum, and vorticity conservation. This increase in vorticity, shockwave frequency and intensity together with the vacuum induced cold boiling of the liquid to be atomized produces an enhanced liquid disintegration action within the vortex accumulation zone 72. This enhanced liquid disintegration thus enables the formulation of small droplets or complete change of phase evidenced by the gasification of liquids and/or the dispersion of fluidized solids.

Fourth, the vortex assembly and accumulation zone 72 at the end of the vortex energy concentration zone 68 efficiently unites the energy in each of the individual vortex flow tubes 58 into one massive three dimensional vortex force field. This vortex force field rotates around the axis of symmetry of the vortex accumulation resonant chamber. The effective total assembled atomizing power of the vortices released into the vortex accumulation zone 72 is much greater than the sum of each of the smaller contributing vortices themselves. Therefore, a three dimensional vortex field of great intensity is created from a series of individual vortices within individual flow tubes 58 which surround a fluid passage 46. The fluid passage 46 delivers the fluid to be atomized to the vortex accumulation zone 72 because of the resultant high vacuum generated therin.

In the vortex accumulation zone 72, downstream from the individual vortex tubes 58, a high vacuum is created. This high vacuum is created by generating a large rotating vortex energy field around the axis of symmetry of the vortex accumulation resonant chamber. A needle valve or electronic flow control device or any other liquid flow control assembly (not shown) on the back end of the vortex rod assembly

40 may be used to precisely control the amount of fluid to be processed by the micro-atomizer. This valve assembly positions the vortex rod assembly 40 within the nozzle body assembly 20. The control of the amount of vortex forming fluid and its characteristic pressure and mass flow passing through the inlet 80 fluid determines the ultimate size of the droplets to be produced by the micro-atomizer of the present invention, as modulated by the amount of fluid to be atomized.

The combination of the coherent vortices in the vortex accumulation zone 72 creates a very large three dimensional rotating stable vortex force field. This three dimensional vortex field produces the vacuum used to draw the fluid to be atomized into the vortex accumulation zone 72 and further includes the shockwaves used to break up the fluids to be atomized into small droplets or disperse fluidized solids.

The volume of the vortex formation zone 62, the number of vortex delivery tubes 58 and the available flow of the vortex forming fluid ultimately determine the amount of fluid that can be micro-atomized as well as the size of the droplets. It has been found that the number of vortex delivery tubes used depends on the mass flow and pressure of the vortex generating fluid, the amount of fluid to be micro-atomized, its density, and the needed energy density of the vortex field to achieve the desired droplet sizes, and resultant terminal velocity etc.

By this combination of the coherent axial rotation of individual vortices in the vortex accumulation zone 72, vacuums between twenty and several hundred inches of water or higher, depending on driving energy (2–20 p.s.i.g.) can be created. The vacuum created is directly proportional to the total mass flow of vortex forming fluid passing through the micro-atomizer as well as the geometry of the zones in which the vortices form and travel. The vacuum created can be used in conjunction with modern solid state pressure sensors to indicate mass flow of the gas powerant or propellant.

As may be seen in FIG. 1, each vortex generating delivery tube 58 fires a high speed vortex into the vortex accumulation zone 72. In addition the high speed vortex includes high frequency shockwaves in the order of 0.1 to 1 MHz. These high frequency shockwaves work together with vortical energies and the high vacuum in the vortex accumulation zone 72 to literally explode the gases entrapped within the fluid and then further to chop liquids into micron size particles regardless of the viscosity of the fluid being atomized. In fact, viscosity which seriously affects prior art mechanical shear atomizers, has no effect at all on the microatomizers of the present invention.

As previously indicated, the terminal energy density of the forces working to micro-atomize a fluid are increased because of a substantial reduction in the area and volumes through which the vortices must travel and the unique properties of vortical flow and conservation of angular momentum. For example, if there were 24 watts total vortex energy to be divided into eight passages, that would result in 3 watts per passage. However, since the diameter of the passage is $1/8$; therefore, there is actually only $1/64$ of the area available for the vortex and $1/512$ the volume. Therefore, the energy area density is actually 24 watts per unit area of passage or nearly eight times the previous area energy density. More significantly, the volumetric energy density is 192 times higher. Additionally, the amount of vortex forming fluid to be processed per unit area is $1/8$th the total amount of liquid. Therefore, there is $1/8$th the amount of fluid to be atomized multiplied by the increased energy density per watt per area. This indicates that there is eight times the magnification factor of 8, or 64 times the gram watts per unit area potential. Even more dramatic and significant is the increase in volumetric energy density—the key performance parameter. This significant increase in vortex energy density happens simply by changing the volume available for vortex travel and the chamber to chamber area ratio and having together with successive multiple vortices which rotate at much higher rotational velocity. All this depends on the successful symbiotic attendant combination of multiple vortices in the vortex accumulation resonant chamber. The use of 8 or 10 or more vortex concentrators considerably enhances the energy coupling efficiency by decade factors. Further, the enhanced rotation impacts the energy process by the square of the rotational velocity increase.

It will be understood that there is no limit to the number, size or shape of individual vortex delivery tubes that can be put together except a physical size requirement associated with a particular application, and the availability of sufficient mass flow in the atomization pressurant fluid. These phenomena and energy couplings are dependent on the generation of stable controlled vortex streams, and the preservation of vorticity.

Referring to FIG. 4, it has been found that the geometry of both a single stable vortex created by an individual vortex delivery tube or barrel 158 and the ring combination is similar to "a Gatling gun", machine gun in physical appearance. Each barrel 158 generates a vortex as a measured amount of vortex forming fluid passes through the barrel. The use of this multiple vortex concentration arrangement provides several other significant utilities.

First, the micro-atomizer can be custom programmed for various liquids or flows by changing the size and number of the vortex forming and focusing rod assembly.

Second, the vortex rod assembly 40 can be moved in a single axis by a small servo-motor to change the rate of flow over to the point of developing a positive pressure to pump a liquid to be atomized back into the container from where the liquid originates and also control the size of the micro-atomized droplets.

Third, any specific application in terms of pressure or mass flow of fluid to be atomized can be quickly and easily customized by modifying the dimensions of the vortex zones to change the energy level.

Fourth, an easily measured and high amplitude vacuum signal is produced by the flow of the vortex forming fluid. This vacuum signal can provide the necessary mass flow information to control the flow rate of the fluid being atomized and gas pressurant mass flow rates. Thus by precise adjustment of a servo motor coupled to a controllable needle valve, a predetermined flow rate can be provided. Accordingly, the micro-atomizer of the present invention is also a mass flow meter, since the process is mass flow driven.

It has been found that relative to other devices, relatively low energy is required to activate the micro-atomization device of the present invention regardless of the flow rate of atomized fluid required. Specifically, the energy required in terms of pressure times volume or mass of material necessary per mass of liquid to be atomized by any comparison to other prior art atomizers is quite low. Pressure and mass are to a large extent interchangeable. It has been found that the amount of energy required to produce effective micro-atomization is from $1/10$ to $1/100$ of prior art atomizers, particularly since prior art microatomizers rely on pressure energy primarily. Similarly, thermal energy or heating can supplement or take the place of pressure and mass flow in terms of energy. Thermal energy is relatively inexpensive and easy to apply to the microatomizer of the present invention especially with current technologies, involving film heaters.

DESCRIPTION OF THE EMBODIMENTS

The operational aspects of the micro-atomizer of the present invention have already been described with respect to FIG. 1. The embodiments which are illustrated in the remaining figures all incorporate the operative principals described with respect to FIG. 1.

FIGS. 2A and 2B illustrate the exterior of the micro-atomizer 10 of the present invention. Note that the operative portions of the micro-atomizer 10 are contained within a nozzle body assembly 20. Intersecting the nozzle body assembly 20 is an inlet tube 80. As may be seen by comparing FIG. 2A and FIG. 2B the inlet tube 80 may either have a straight end portion 81 or a threaded end portion 82. The inlet tube 80 intersects the cylindrical section 22 of the nozzle body assembly 20. Located on one end of the nozzle body assembly 20 is an adjustment knob 42 that may be used to turn the vortex rod assembly 40 by the threadable engagement of the rod displacement threads 44 (FIG. 2C) with the threads that are formed on the interior of the cylindrical section 22 of the nozzle body assembly 20. On the opposite end of t he nozzle body assembly 20 from the adjustment knob 42 is a vortex accumulation resonant chamber 70 whose function will be explained below. By specific reference to FIG. 2B it may be seen that by looking into the micro-atomizer through the resonator assembly 70, the individual vortex delivery passages or energy density concentration channels 58 may be seen on the end of vortex rod assembly 40.

The inside the micro-atomizer 10 of the present invention may be understood by reference to FIG. 2C. As shown in FIGS. 2A and 2B, an inlet tube 80 intersects the cylindrical section 22 of nozzle body assembly 20. An adjustment knob 42 appears on one end of the cylindrical section 22 of nozzle body assembly 20 and vortex accumulation resonant chamber 70 appears on the opposite end. Moving within the interior of the cylindrical section 22 of nozzle body assembly 20 is a vortex rod assembly 40. The vortex rod assembly 40 is moved by interengagement of the rod displacement threads 44 with the internally threaded section 24.

Within the cylindrical section 22 of nozzle body assembly 20 are formed several distinct sections. In the midst of the cylindrical section 22 is a central cylindrical portion 26. This central cylindrical portion 26 ends in a taper 28. Downstream from the taper 28 is a forward cylindrical section 30. The forward cylindrical section 30 continues into the vortex concentration passage section 32. Th e vortex concentration passage section 32 continues into the resonator mounting section 34. Intersecting the central cylindrical portion 26 is a bore 36 for the positioning of an insert mounting 86 which positions the inlet tube 80 on the nozzle body assembly 20. The inlet tube 80 allows for fluid communication of the hollow portion 84 of the inlet tube 80 with the central cylindrical portion 26 of the nozzle body assembly 20.

The vortex rod assembly 40 has a rear taper 48 formed adjacent the rod displacement threads 44. Downstream from the rear taper 48 is a large cylindrical section 50 which terminates at forward taper 52. Following the forward taper 52 is a reduced cylindrical portion 54. Following the reduced cylindrical portion 54 is a fluted section 56. The fluted section 56 fits snugly within the vortex concentration passage section 32. Downstream from the fluted section 56 is the vortex accumulation resonant chamber 70 which includes a cylindrical bore 74 and a tapered bore 76.

Proceeding on to FIG. 3 it may be seen how the vortex rod assembly 40 moves within the nozzle body assembly 20. By axially moving the vortex forming adjustment knob 42 the vortex rod assembly 40 may be moved axially within the bore of nozzle body assembly 20. This movement of the vortex rod assembly 40 changes the size of the interior chamber 60 which is formed between the vortex rod assembly 40 and the nozzle body assembly 20. The change in the shape of the interior chamber 60 effects the formation of the vortices around the large cylindrical section 50 of the vortex rod assembly 40. The movement of the vortex rod assembly 40 also changes the pressure drop through the interior chamber 60 and thus the gas mass flow, resultant energy generation and vortex vacuum, thus liquid flow rate. As fluid pressure causes the vortices to pass from the vortex formation zone 62 into the vortex concentration zone 64 and then into the vortex organization zone 66, the vortices encounter the flutes 55. This causes the individual vortices to then be channeled through the individual vortex energy amplification and concentration channels 58 through entry port 57 where their energy density is substantially concentrated. After exiting the individual vortex energy amplification and concentration channel 58 through the exit port 59 the vortices come together in the vortex accumulation zone 72 formed within the vortex accumulation resonant chamber 70. Note that in FIG. 3 the vortex accumulation resonant chamber 70 is made a part of the nozzle body assembly 20. It is in the vortex accumulation zone 72 that the high vacuum is created which draws the fluid to be atomized through the fluid passage 46 and out through the outlet port of the fluid passage 47. Shockwaves formed within the individual vortex delivery passages 58 proceed into the vortex accumulation zone 72 and the combination of shockwaves, high speed vortex dynamics, centripetal forces come together synergistically to make small droplets or gasify the fluid to be atomized or disperse a flowable solid. The illustrated embodiment has been found to work best with a broad variety of flows of the vortex forming fluid.

In FIG. 4 a second embodiment or a "gatling gun" version 110 of the micro-atomizer of the present invention is shown. Note that the micro-atomizer nozzle body assembly 20 is essentially the same as shown in FIG. 3 but for having a separate vortex accumulation resonant chamber 70. Accordingly, the same reference numbers are used to describe the nozzle body assembly 20. However, as the vortex rod assembly 140 is different a "1" has been inserted in the hundreds place. The remainder of the reference numbers relate to items having a similar function and location as in FIG. 3.

The difference between the embodiment with the individual flutes 55 shown in FIG. 3 and the embodiment shown in FIG. 4 is the configuration and shape of the individual vortex energy amplification and concentration channels 158. Note that instead of having "u"-shaped channels as shown in FIG. 3, each vortex delivery passage is a hollow cylinder. While circular passages have been shown, it will be understood that a broad variety of different shaped passages may be used. Because a broad variety of different shaped passages may be used, the problem of using laser drilling or exotic molding techniques to make small holes is effectively eliminated. The rotation of the moving vortices tends to center itself in any geometrically shaped passage such as a cylinder, triangle or rectangle, a unique property of vortical flows. Thus, as vortices are formed alongside the large cylindrical section 150 of the vortex rod assembly 140 in front of the rear taper 148 they pass along the forward taper 152 of the vortex rod assembly 140 on their way to the exterior of the reduced cylindrical portion 154. It is there they pass through entry port 157 into the individual vortex delivery passages 158 in the cylindrical passageway section 156 of the vortex rod assembly 140. The vortices exit the individual vortex delivery passages 158 through the exit port 159. From there they pass into the vortex accumulation zone 72 in the vortex accumulation resonant chamber 70. The fluid to be atomized enters the vortex accumulation zone 72 through a higher volume outlet port 147. This embodiment works best with higher mass flows of vortex forming fluid. It can also be delivered through several tubes as well.

Figure 3:
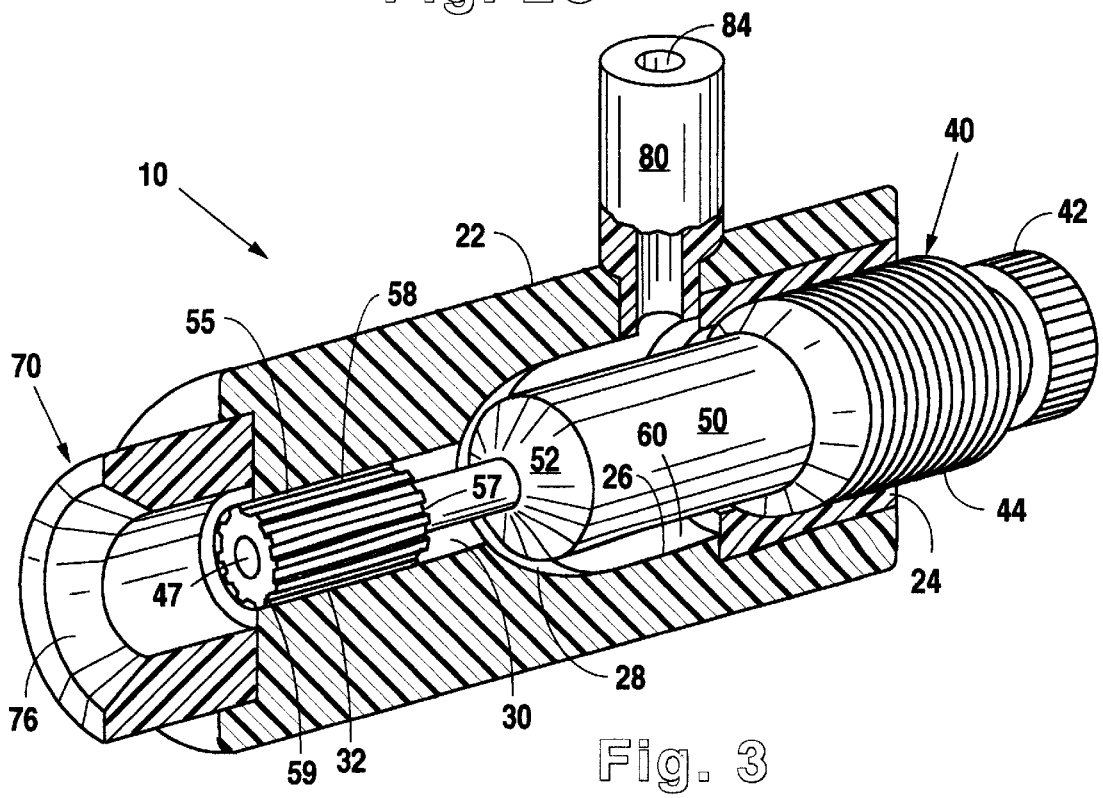
FIG. 3 is a perspective view in partial section of a micro-atomizer having a fluted dumb bell vortex rod assembly.

In FIG. 5 yet another embodiment 210 of the micro-atomizer device of the present invention is shown. Note that there are several differences between this embodiment and the embodiments shown in FIGS. 3 and 4. However, items having a similar location and function have the same reference number as in earlier figures but for the "2" in the hundreds place.

On the nozzle body assembly 220 the inlet for liquid or powder 237 to be atomized is substantially perpendicular to the long axis of the nozzle body assembly 220. Additionally, multiple radial passages 277 and an intersecting axial passages 279 are formed in the rear of the resonator assembly.

The vortex rod assembly 240 shown in FIG. 5 also has several distinct differences. At its rear portion a reduced rear cylindrical portion 243 is included. This reduced rear cylindrical portion 243 is in fluid contact with the hollow portion 238 of the liquid or powder inlet 237. A liquid inlet bore 245 is formed in the reduced rear cylindrical portion 243 to allow the passage of the liquid or powder to be atomized into the fluid passage 246 which runs through the center portion of the vortex rod assembly 240. To stop fluid leakage the reduced rear cylindrical portion 243 is sealed against the inside of the nozzle body assembly 220 by packing rings 249 which are adjacent the guide sections 244.

It will be noted that as the small vortices are formed in the chamber 260 formed between the vortex rod assembly 240 and the nozzle body assembly 220 these small vortices travel as in the prior embodiments. Specifically, the vortices form in the large cylindrical section 250 in the central cylindrical section 226. The vortices are then concentrated over taper 252 in the taper section 228. Next, the vortices are organized over reduced cylindrical portion 254. The vortices are then concentrated by proceeding through one of a plurality of axial passageways 279 and then through the intersecting radial passageways 277. The vortices then proceed through the annular vortex delivery passage 258 into the vortex accumulation zone formed in the vortex accumulation resonant chamber 270. The fluid to be atomized or flowable solid to be dispersed is drawn through outlet port 247.

In FIG. 6 an adaptation 310 of the instant invention used to atomize fuel for burning is shown. Items having a similar location and function have the same reference numbers as in the earlier figures but for a "3" in the hundreds place. A blower 312 is placed at the inlet 380 to the nozzle body assembly 320. Fuel enters the central passage 346 through fuel inlet 314. A mounting flange 316 allows the combustion atomizer 310 of the present invention to be utilized in a fixed installation. An extension is formed at the downstream end of the vortex accumulation resonant chamber 370. A flame is propagated in the area designated by reference number 319.

Shown in FIGS. 7A, 7B, 7C and 7D is a somewhat different micro-atomizer 410 according to the present invention in a configuration to be an aerosol powered utilizing a pressurized liquid propellant driven medicament atomizer. Those items which have similar characteristics and placement to those items found in prior embodiments have the same numbers but for the number "4" placed in the hundreds place.

In this special version of the multiport micro-atomizer, the liquid to be atomized and the gas powerant are both uniquely moved through the vortex forming, shockwave geometries. Such devices are applicable to pressurized liquid propellant applications only, be they for delivery of medicaments or for use in aerosol delivery systems. The amount of fluid to be micro-atomized is small. The operation usually is pulsed.

In addition, this device incorporates a special vortex accumulation chamber and special additional geometries to uniquely and substantially reduce the existing velocity of the exiting micro-atomized fluid to $\frac{1}{8}$ to $\frac{1}{10}$ its normal speed to efficiently allow the delivery of drugs to the alveolar lung tissue.

In addition, due to the limited mass of gas available per actuation of the device, a unique three-part vortex intensifier is employed. Again, two large members, male and female, with unique triangular geometry are used.

The medicament metered dose inhaler micro-atomizer is shown in its complete form in FIG. 7A. Note that an aerosol metered vial 412 is contained in a shell 413 at the rear end of the micro-atomizer 410. It contains pressurized liquid propellant and medicine. Medicament passes through a mouthpiece or nasal adapter 416 into the patient. In this embodiment, both the propellant, in this case a pressurized high density freon propellant, and the medicament both flow together through the vortex forming and intensifying geometries.

By reference to FIG. 7B it may be seen that the aerosol metered dose vial 412 feeds a pressurized gas combined with and containing medicament into the rear end of the micro-atomizer 410. The pressurized gas and medicament then exits the micro-atomizer 410 through a vortex accumulation resonant chamber 470 before passing through a special geometry to cause a material deceleration which is $\frac{1}{8}$ to $\frac{1}{10}$ of prior art device speeds, in passing through deceleration zone 418 on its way to a mouthpiece adapter 419. If desired, a nasal adapter 411 may be attached over the mouthpiece adapter 419. The deceleration zone 418 and attendant geometry is vital for proper drug delivery. It prevents normal uncomfortable cold blast, inertial impaction, or the failure of drug to round the right angle turn in the larynx and reach the alveolar lung tissue generated by prior art medicament atomizers, which prior art medicament atomizers produce high speeds, cold blast, inertial impaction, patient discomfort, and difficulty in patient inhalation and drug synchronization.

The actual arrangement of the three passage vortex system concentration may be seen by reference to FIGS. 7C and 7D. Therein the vortex rod assembly 440 is shown in the midst of a nozzle body assembly 420. As in all other vortex micro-atomizers where in vortex concentrators, the vortices are formed and concentrated in the vortex accumulation zone, but in this case where the medicament to be atomized is also combined with the powerant fluid, the contents of the aerosol metered vial 412 containing both are caused to pass through multiple individual vortex delivery passages 458. It is in these individual passages 458 that the energy density of the flowing fluid is concentrated. For low flows, an equilateral triangle-shaped passage 458 has proven to be the most effective. Prior art devices always feature a single passage or delivery port. As the medicament enters the vortex accumulation resonant chamber 470 a vortex force field and a vacuum will be formed which vortex field and vacuum micro-atomizes and draws additional outside entrainment air through the micro-atomizer 410. The vortex field and the shockwaves within the vortex accumulation resonant chamber 470 form small droplets or gasify the medicament and reduce its speed for administration at a substantially slow rate to allow proper medicine absorption in the lungs not in the back of the throat. It has been found that this embodiment produces much more uniform microdispersed droplets and much lower speed delivery to the lungs, and not to the larynx, stomach, or other undesirable areas in the patient as do the prior art atomizers of this type. All of the design geometries are necessary to achieve this goal.

Figure 8A:
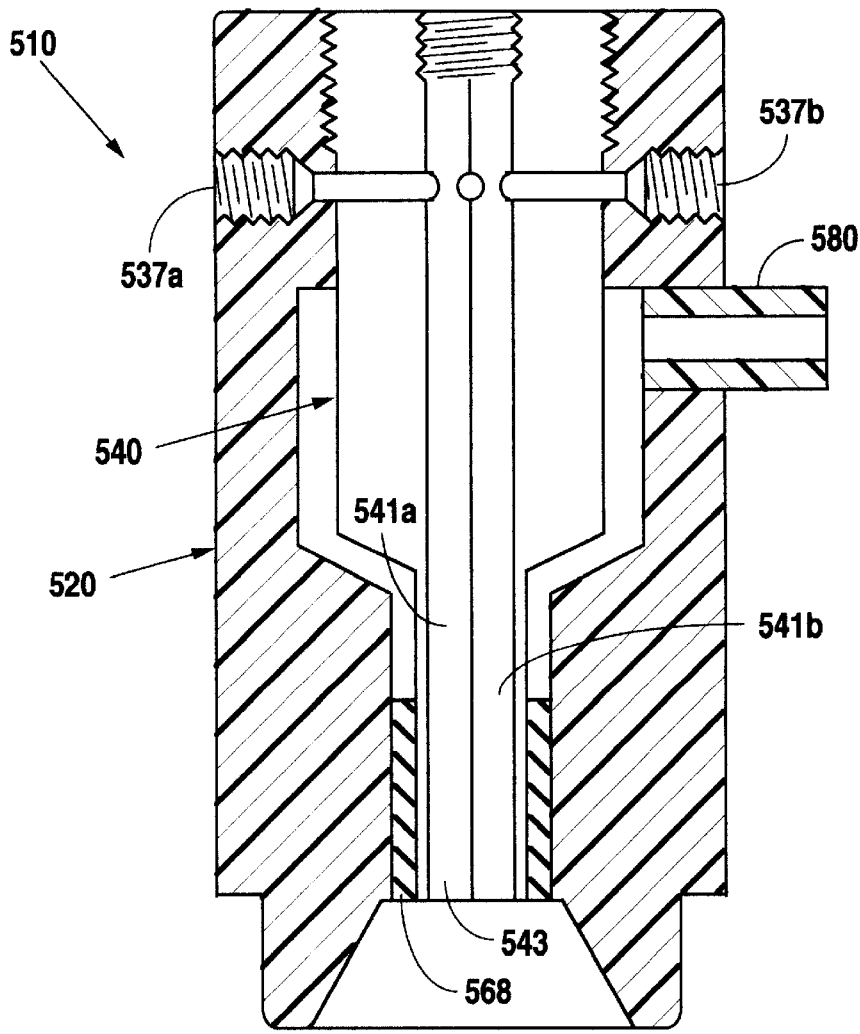
FIG. 8A is a series of drawings of a micro-atomizer according to the present invention used for mixing at least two fluids.
Figure 8B:
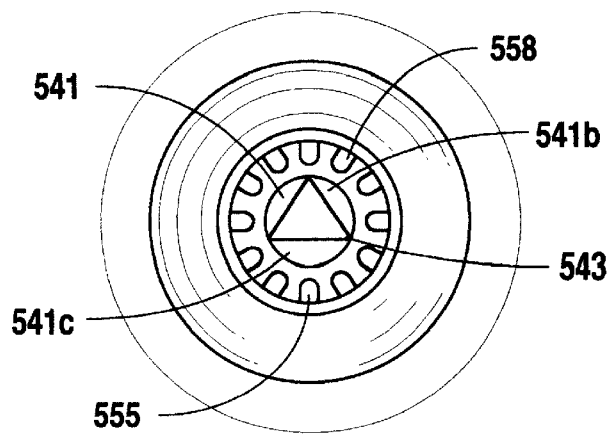
FIG. 8B is an end view of the micro-atomizer shown in FIG. 8A.

In FIGS. 8A and 8B an embodiment 510 of the present invention is shown which mixes two or more liquids as they are being atomized. Items which have a similar location and function have the same reference numbers as in the earlier figures but for a "5" in the hundreds place. The nozzle body assembly 520 includes inlet passageways 537a and 537b for the entry of multiple liquids to be atomized or powders to be dispersed. Inlets 537a and 537b are in contact with liquid paths 541a and 541b respectively which are formed on the exterior of flow separator 543. In the embodiment shown, a third liquid path 541c is also shown for the combination of three fluids. The remainder of the operation of this embodiment is shown in the prior figures but for the fact that three separate substances pass into the vortex accumulation resonant chamber 520. The high speed vortices and shockwaves within the vortex accumulation resonant chamber 570 both micro-atomize and disperse the various fluids as well as intermixing the atomized and dispersed substances together, or react them chemically.

Figure 9A:
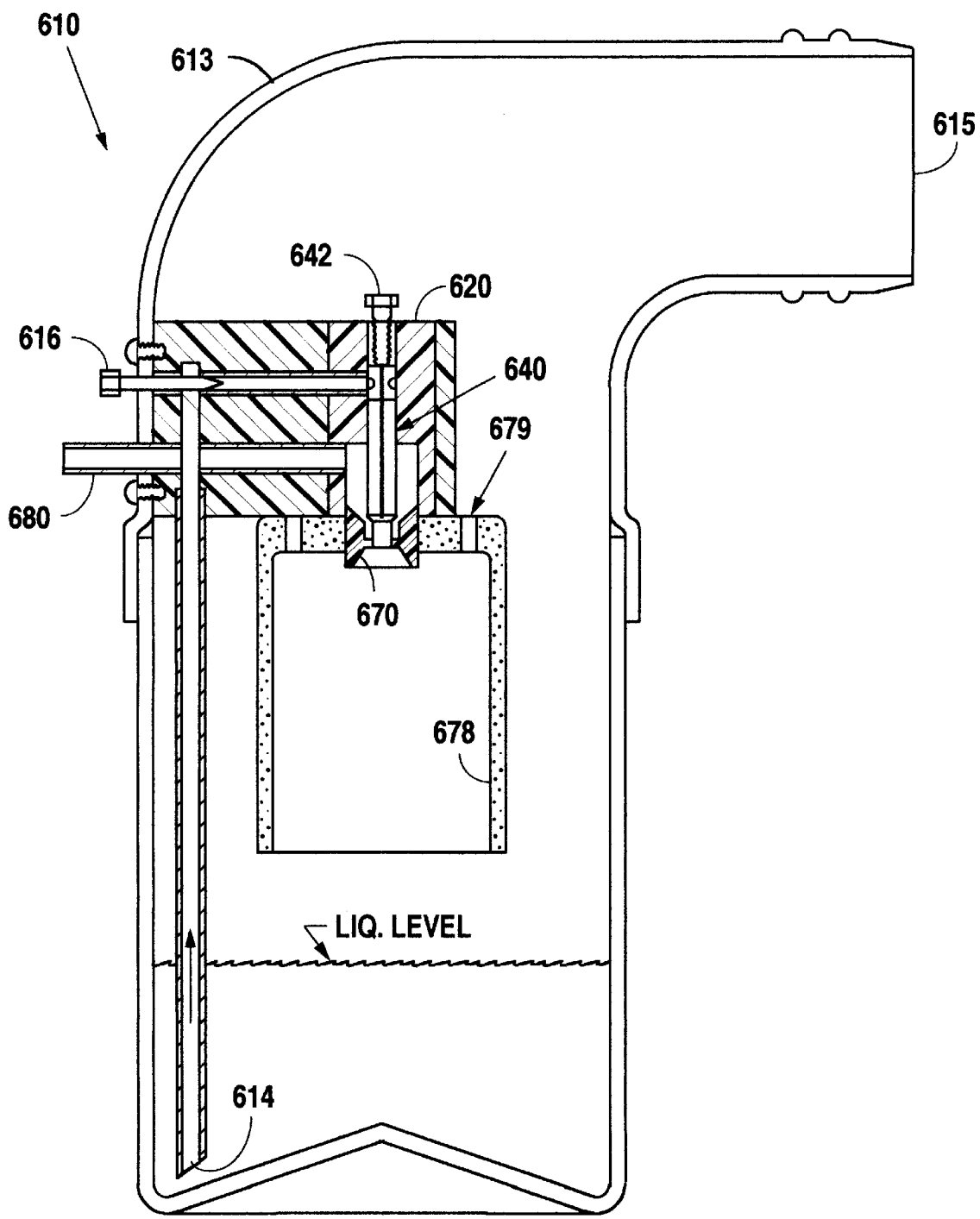
FIG. 9A is an elevational view in partial section of a nebulizer resonant chamber according to the present invention.
Figure 9B:
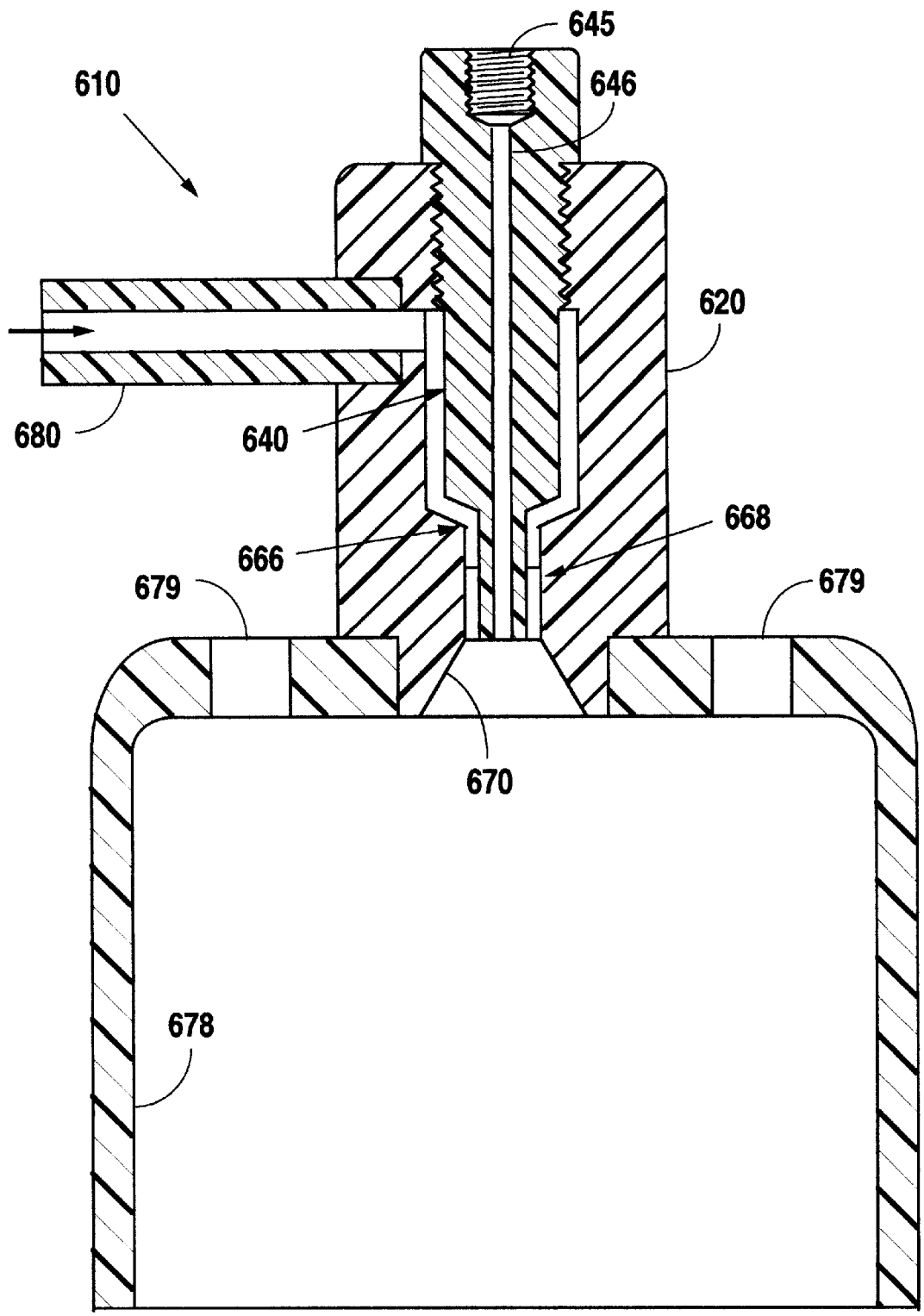
FIG. 9B is an enlarged view of the nebulizer shown in FIG. 9A except for an inline liquid inlet.

In FIGS. 9A and 9B a nebulizer assembly 610 is shown. Items having a similar location and operation bear the same reference numbers as in earlier embodiments but for the "6" in the hundreds place. By specific reference to FIG. 9A it is seen that fluid is drawn out of a liquid storage area, through liquid inlet 614, and past liquid flow adjustment valve 616 on its way to operative portion of the micro-atomizer of the present invention. The fluid is then drawn through the micro-atomizer of the present invention as shown in previous embodiments by the vortices formed in the vortex forming liquid which enters the micro-atomizer through inlet 680. The nebulizer of the present invention is mounted in a housing 613 having an outlet 615. A closer view of the micro-atomizer, as utilized in the nebulizer assembly 610 shown in FIG. 9A, appears in FIG. 9B. Note that a vortex receiving zone 678 is formed downstream from the vortex accumulation resonant chamber 670. Note also that in FIG. 9B the entry of the fluid to be atomized does not enter the micro-atomizer radial to the long axis of the micro-atomizer as shown in FIG. 9A but rather enters axially. Prior art medical nebulizers produce both large and small droplets which must be separated or baffled. No such separation of droplets is required in the nebulizer incorporating the micro-atomizer of the present invention. In many cases, prior art nebulizers require high pressure.

Figure 10:
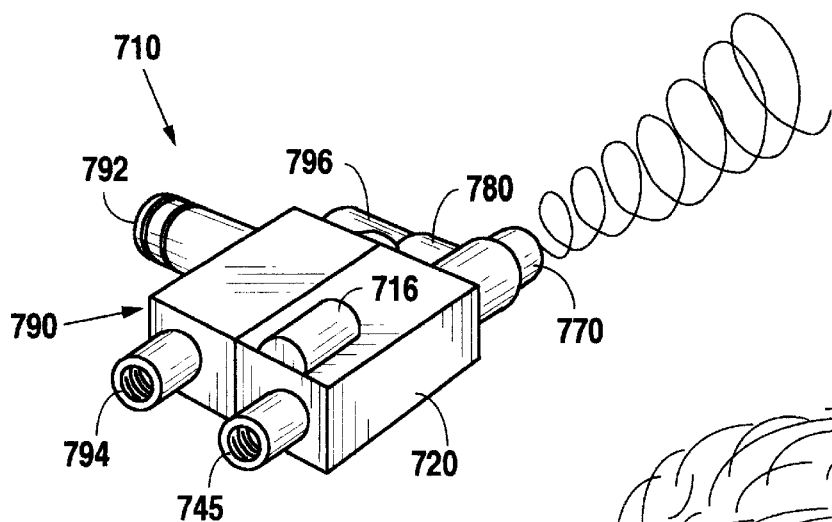
FIG. 10 is a perspective view of a micro-atomizer according to the present invention mounted alongside a precision flow meter.

In FIG. 10 yet another embodiment 710 of the present invention is shown. Items having a similar location and function bear the same reference number as in prior embodiments but for the "7" in the hundreds place. Herein the micro-atomizer of the present invention 710 is shown in conjunction with a precise mass flowmeter 790 similar to that described in my copending application which is incorporated by reference herein. The liquid to be atomized enters through inlet 745. Precise control of the vortex forming liquid is obtained by utilization of the flowmeter output control 792 which causes a precise amount of vortex forming liquid to be passed through conduit 796 into the micro-atomizer of the present invention. A signal from the precision flowmeter 790 may also be sent to a servo motor to control the position of the nozzle rod assembly in the nozzle body assembly. By such precise control of fluid flow a very precise micro-atomization pattern and quantity of fluid delivered can be obtained.

Figure 11A:
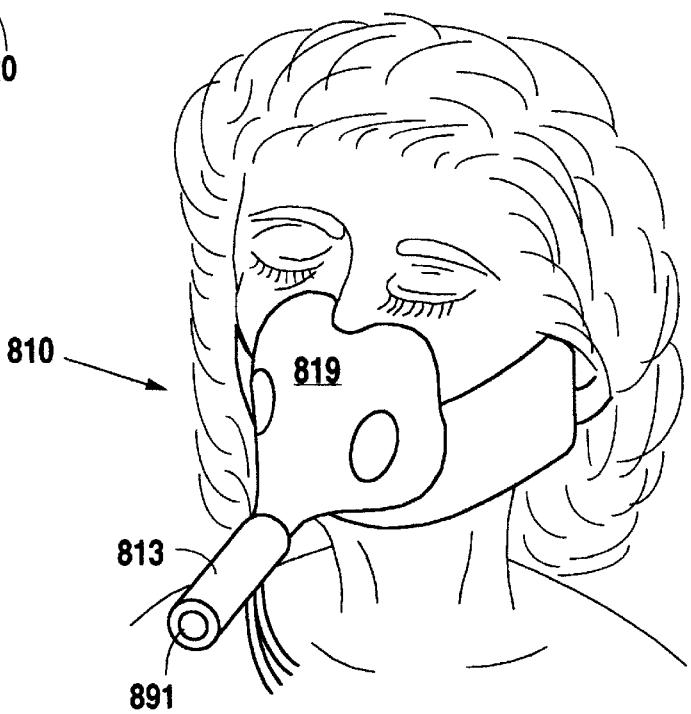
FIG. 11A is a perspective view of a mask atomizer according to the present invention installed on a patient.
Figure 11B:
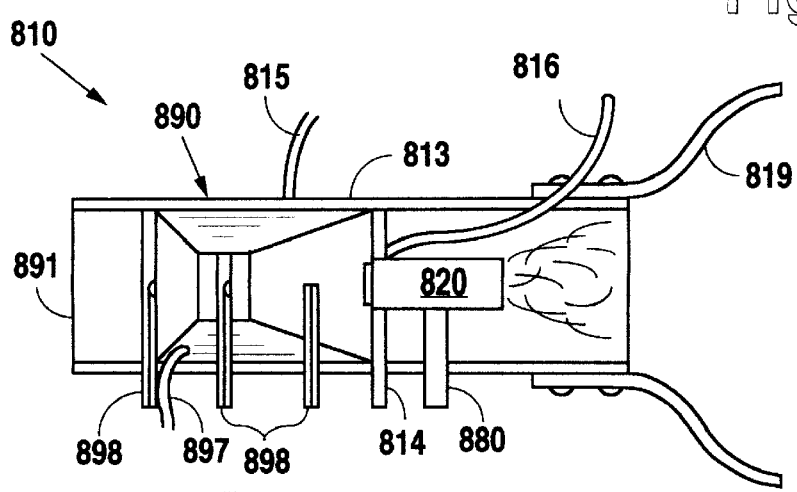
FIG. 11B is a cross-sectional view of the mask atomizer shown in FIG. 11A.

FIGS. 11A and 11B show a patient mask mounted atomizer 810. Items having a similar location and function bear the reference numbers as in prior embodiments but for the number "8" in the hundreds place. The mask mounted atomizer 810 is also used in conjunction with a precise vortex mass flowmeter assembly 890 as in FIG. 10. Within the flowmeter assembly 890 are flow rods 898 which precisely monitor the flow through the flowmeter assembly 890. In this embodiment 810, oxygen may be used as a vortex forming fluid as it enters through inlet 880. If desired, a flow signal indicating liquid delivery may be obtained from a probe as shown at reference number 816. An oxygen flow signal can be obtained from another probe as shown at reference number 815. If desired, the gas may be heated by a heater inserted as shown at reference number 897. The exiting micro-atomized fluid passes through a mask 819 into the mouth and nasal passages of a patient. This device can also be used with breathing aid devices, respirators, ventilators and apnea devices such as B-PAP devices.

Key Advantages

The micro-atomizer of the present invention does not utilize mechanical fluid shearing caused by high pressure gases or liquids and high velocity flow used in almost all current atomizers which absence of mechanical fluid shearing thus reduces the possibility of damage to the atomized product and has eliminated clogging. None of the fluid to be atomized flows in the vortex forming passages. The only disclosed exception is this invention's metered dose inhaler version in which the small amount of medicament and vortex action maintain cleanliness within the vortex forming passages. This is particularly important where a genetically engineered material or delicate chemical compounds are to be atomized. In chemical processes micro-atomized catalysts will enable faster more efficient reactions because of the greater dispersion of catalysts (catalysts are generally expensive) in the reacting chemicals. Also in combining chemical compounds, both micro-atomization and the dynamic motion of the vortex force field aides and abets these processes materially.

The micro-atomization device of the present invention may also be utilized without concern with fluids having a wide variety of densities and viscosities. Typically, prior art atomizers have difficulty or fail when atomizing fluids with high densities and viscosities. Specifically, prior art atomizers require square law increases in pressure proportional to these two parameters. In addition, such fluids need to be forced through small holes to be atomized at all in the prior art atomizers with the resultant shear atomization effect. No such tortuous passage of the fluid to be atomized occurs through small holes or passages is required in the present invention, nor does the fluid to be atomized have to pass through these small passages or holes. In this invention, atomization uniquely occurs in three dimensional force fields in the open space of the vortex accumulation resonant chamber.

The high vacuum created in the vortex accumulation resonant chamber aside from the transport of fluid and the effects of cold boiling also provides usable signals which can readily be used for mass flow measurement of and thus the electronic control of the input of vortex forming fluids or the fluid to be atomized and thus the control the entire micro-atomizing process.

Because there is no liquid flow in the energy generation portion of the micro-atomizer of the present invention except for metered dose inhalers, there is no opportunity for clogging of the flow passages within the micro-atomizer or conflict with the vortex generating process. Additionally, there is no atomizing product accumulation or any requirement to clean the device. The device is self-cleaning, in most applications, due to the cleaning action of the rotating vortex.

Precise mass flow information can be provided inherently by generating mass related signals as the micro-atomizer of the present invention operates, since all vortex devices are mass driven and responsive.

Very low forward speed micro atomization flows are possible. Additionally, the flow of fluid can be softened and changed to a variety of different patterns as shown in medicament atomizer illustrated in FIGS. 7A, 7B, 7C and 7D.

Fuels may be turned directly into gaseous or near gaseous states. A gaseous state is particularly desirable when injecting fuel directly into combustion chambers with the vastly enhanced ability of the fuel to entrap air for combustion. Greater efficiencies can be obtained if engine exhaust gases are used to power the vortices to micro-atomize and mix the mixture of fuel and air gases. And if the fuel is additionally injected directly into combustion chambers, emissions can be cut substantially. Engine heat may be used to add substantive efficiency to the process as well.

Water based paints or coatings may be micro-atomized easily as the powerful shockwaves and cold boiling used to form droplets have enough force to break through the high surface tension of water droplets. In addition, highly viscous fluids used in coating processes such as primers or adhesives may be micro-atomized, with no concern about their viscosity.

Intersecting arrays of vortices may be established to mix fluids as shown in FIGS. 8A and 8B or intensify the energy process by increasing the number of microatomization devices.

In still other embodiments in the present invention, servo mechanisms may be incorporated to precisely move the dumbbell shaped vortex rod assembly within the nozzle body assembly to adjust liquid and gas flow rates or droplet size of the micro-atomized liquid.

Thermal energy may be added to the vortex forming fluids with simple film heating devices to substantially increase the energy output of the micro-atomizing devices. Products of combustion and steam can be used to intensify and power more powerful devices.

The major heat transfer cooling effects of the micro-atomizer of the present invention allows it to be used in dispensing heated fluids or liquified dispersing metals into powders, or in the manufacture of polyester material or in the manufacture of metalized powders. The micro-atomizer of the present invention can also be used to augment modern air conditioning processes and enhance the effectiveness of the new lower efficiency refrigerants.

The utility of the present invention with water is of particular significance. Heated water may be rapidly cooled thus permitting higher efficiencies when first stage water cooling is used in new generation air conditioning systems. Contaminants may be easily separated from water during the micro-atomization process. Sea water may also be desalinated by the micro-atomization of the present invention, with less energy due to efficient energy coupling, and greater surface area of the vaporous output.

Experimental use has shown that the size of the droplets produced by the micro-atomizer of the present invention has a significantly more uniform distribution than that available with the prior art microatomizers, namely monodispersed droplets (limited size range) versus the usual bell shaped distribution curve of droplet size.

The concentrated high energy field produced by the micro-atomizer of the present invention also has use in situations characterized by extraordinary heat transfer capabilities, such as are found in normal industrial heating and cooling systems. Heat can also be used as the primary power source as is mass flow and pressure normally. Steam is an ideal vortex forming fluid. In addition the micro-atomizer of the present invention may be used for the fluidization of powders and hybrid liquids, the activation of catalysts, the activation of both chemical and organic catalysts, in multi-component chemical reactors, the spray drying and flavoring of foods, and the spray drying of chemicals and pharmaceutical powders for drug manufacture.

The unusual nature of vortex and shockwave energy provided by the micro-atomization system of the present invention allows it to be used not only for the atomization of liquids but also the dispersal of particles of solid matter to include fluidized powders such as powdered coal, powdered paints or coatings, powdered drugs and/or hybrid compounds.

Either steam or compressed air may be used as the vortex forming fluid for the liquid to be micro atomized. Because of the thermal energy in steam and because of its higher mass density and viscosity, steam is a preferred working fluid, particularly for industrial applicators. Heat also enhances gas viscosity and thus the efficiency of the vortex formation process.

The nozzle body and vortex rod may be formed from metal, plastic or ceramic.

While the invention has been described by reference to its preferred and alternate embodiments, those of ordinary skill in the art will understand that numerous other embodiments are possible. Such numerous other embodiments shall fall within the scope of the appended claims.

I claim:

1. A micro-atomizing device comprising:
   a fluid conduit having an outer chamber and an inner channel;
   means for forming moving vortices in a first fluid in said outer chamber of said fluid conduit;
   a plurality of passages within said fluid conduit constructed and arranged to geometrically reduce the areas and volumes to intensify said moving vortices;
   said plurality of passages being in fluid communication with a vortex accumulation resonant chamber;
   said inner channel being constructed and arranged to conduct a second fluid through said fluid conduit into said vortex accumulation resonant chamber;
   whereby the accumulation of said moving vortices in said vortex accumulation resonant chamber creates a high vacuum force field including shockwaves such that said high vacuum force field draws said second fluid through said inner channel, induces cold boiling of said second fluid, and said shockwaves further micro-atomize said second fluid into droplets within said vortex accumulation resonant chamber.

2. The micro-atomizing device as defined in claim 1 wherein said fluid conduit is a nozzle body assembly having:

an inlet for the passage of said first fluid into said outer chamber;

said outer chamber forming:

a vortex formation zone;

a vortex concentration zone downstream from said vortex formation zone;

a vortex organization zone downstream from said vortex concentration zone;

said vortex organization zone being upstream from said plurality of passages.

3. The micro-atomizing device as defined in claim 2 wherein said nozzle body assembly further includes a large central section for the formation of said moving vortices, a tapered section for the concentration of said moving vortices and a second cylindral section for the organization of said moving vortices and a section for the placement of plurality of passages.

4. The micro-atomizing device as defined in claim 3 wherein said vortex accumulation zone is formed in a vortex accumulation resonant chamber.

5. The micro-atomizing device as defined in claim 4 wherein said nozzle body further includes a vortex rod assembly constructed and arranged to mount within said nozzle body and, in conjunction with said nozzle body assembly, to form said vortex formation zone, said vortex concentration zone, in said vortex organization zone.

6. The micro-atomizing device as defined in claim 5 wherein said vortex rod assembly is adjustably positioned within said nozzle body assembly.

7. The micro-atomizing device as defined in claim 6 wherein the flow of fluid to be atomized is controlled by adjusting the position of said vortex rod assembly within said nozzle body assembly.

8. The micro-atomizing device as defined in claim 7 wherein the position of said vortex rod assembly within said nozzle body assembly is controlled by a servo motor.

9. The micro-atomizing device as defined in claim 5 wherein said vortex rod assembly includes said inner channel.

10. The micro-atomizing device as defined in claim 5 wherein said vortex rod assembly includes a large cylindrical section which, in conjunction with said large cylindrical section of said nozzle body assembly, form said vortex formation zone.

11. The micro-atomizing device as defined in claim 10 wherein said vortex assembly further includes a tapered section which, in conjunction with said tapered section of said nozzle body assembly, forms said vortex concentration zone.

12. The micro-atomizing device as defined in claim 11 wherein said vortex rod assembly includes a reduced cylindrical portion which, in conjunction with said second cylindrical section of said nozzle body assembly, forms said vortex organization zone.

13. The micro-atomizing device as defined in claim 12 wherein said plurality of passages are formed between said vortex rod assembly and said nozzle body assembly.

14. The micro-atomizing device as defined in claim 12 wherein said plurality of passages are formed in said vortex rod assembly.

15. The micro-atomizing device as defined in claim 13 wherein said plurality of passages are formed in said vortex rod assembly.

16. The micro-atomizing device as defined in claim 14 wherein said plurality of passages are substantially cylindrical openings through a cylindrical section of said vortex rod assembly to increase the energy concentration of said moving vortices.

17. The micro-atomizing device as defined in claim 12 wherein said plurality of passages are annular spaces between said vortex rod assembly and said nozzle body assembly.

18. The micro-atomizing device as defined in claim 1 wherein said droplets are substantially uniform in size.

19. A micro-atomizing device for the micro-atomization or gasification of fuels comprising:

a blower assembly;

a source of liquid fuel or powdered solid fuel;

a hollow nozzle body having an inlet in fluid connection with said blower assembly;

a vortex rod assembly having a fuel flow passage therethrough, said vortex rod assembly constructed and arranged to mount within said hollow nozzle body;

said hollow nozzle body in said vortex rod assembly forming a vortex formation zone downstream from said inlet within said hollow nozzle body;

a vortex concentration zone downstream from said vortex formation zone;

a vortex organization zone downstream from said vortex concentration zone;

a plurality of vortex energy density concentration zones downstream from said vortex organization zone;

said plurality of vortex energy density concentration zones constructed and arranged to increase the rotational speed of said vortices;

a vortex accumulation resonant chamber downstream from said plurality of vortex energy density concentration zones;

said vortex accumulation resonant chamber enabling the formation of a vacuum force field with shockwaves contained therein;

whereby fuel is drawn through said fuel flow passage by said vacuum force field into said vortex accumulation resonant chamber, cause to cold boil and did cause to form droplets or gas by said shockwaves.

20. The micro-atomizing device as defined in claim 19 further including a decelerator extension piece downstream from said vortex accumulation resonant chamber.

21. A micro-atomizing device for delivering medicaments comprising:

a metered dose aerosol vial containing a medicament and a propellant;

a hollow nozzle body having a substantially radial inlet in fluid communication with said metered dose aerosol vial;

a vortex rod assembly constructed and arranged to mount within said hollow nozzle body;

said hollow nozzle body in said vortex rod assembly forming a vortex formation zone downstream from said substantially radial inlet within said hollow nozzle body;

a vortex concentration zone downstream from said vortex formation zone producing at least three vortex concentrations;

a vortex energy density concentration zone downstream from said vortex concentration zone having a substantially triangular geometry;

a vortex accumulation resonant chamber downstream from said vortex energy density concentration zone in which the medicament is micro-atomized;

a deceleration zone downstream from said vortex accumulation resonant chamber.

22. The micro-atomizing device for delivering medication as defined in claim 21 further including a mouthpiece downstream from said deceleration zone.

23. The micro-atomizing device for delivering medication as defined in claim 22 further including an adapter for fitting into a nasal passage, said adapter being positioned downstream from said deceleration zone.

24. The micro-atomizing device for delivering medication as defined in claim 22 wherein the medicament is a fluid, a powder, or a combination thereof.

25. The micro-atomizing device for delivering medication as defined in claim 22 in which said propellant flows together with a micro-atomized medicament.

26. A micro-atomizing device for combining a plurality of liquids comprising:

a hollow nozzle body;

a vortex rod assembly constructed and arranged to adjustably mount within said hollow nozzle body;

said vortex rod assembly having a central fluid flow passage therethrough;

said central fluid flow passage having a channel and an entry port for each of said plurality of liquids to be mixed;

said hollow nozzle body having an inlet in fluid communication with each of said entry ports;

said hollow nozzle body having an inlet for a vortex forming fluid;

said hollow nozzle body in said vortex assembly rod forming a zone for the generation of vortices in said vortex forming fluid downstream from said inlet;

said hollow nozzle body in said vortex rod assembly forming a zone for the concentration of vortices in said vortex forming fluid downstream from said zone for the generation of vortices;

said hollow nozzle body in said vortex rod assembly forming a zone for the organization of vortices in said vortex forming fluid downstream from said zone for the concentration of vortices;

said hollow nozzle body in said vortex rod assembly forming a zone for the energy density concentration of said vortices downstream from said zone for the concentration of vortices;

said hollow nozzle body forming a zone for the accumulation of vortices downstream from said zone for the energy density concentration of said vortices;

said zone for the accumulation of vortices characterized as including a high vacuum force field and shockwaves;

whereby said plurality of fluids may be drawn through said channels by said high vacuum force into said zone for the accumulation of vortices and atomized in said zone for the accumulation of vortices by said shockwaves and thereby mixed together or chemically reacted.

* * * * *